United States Patent [19]

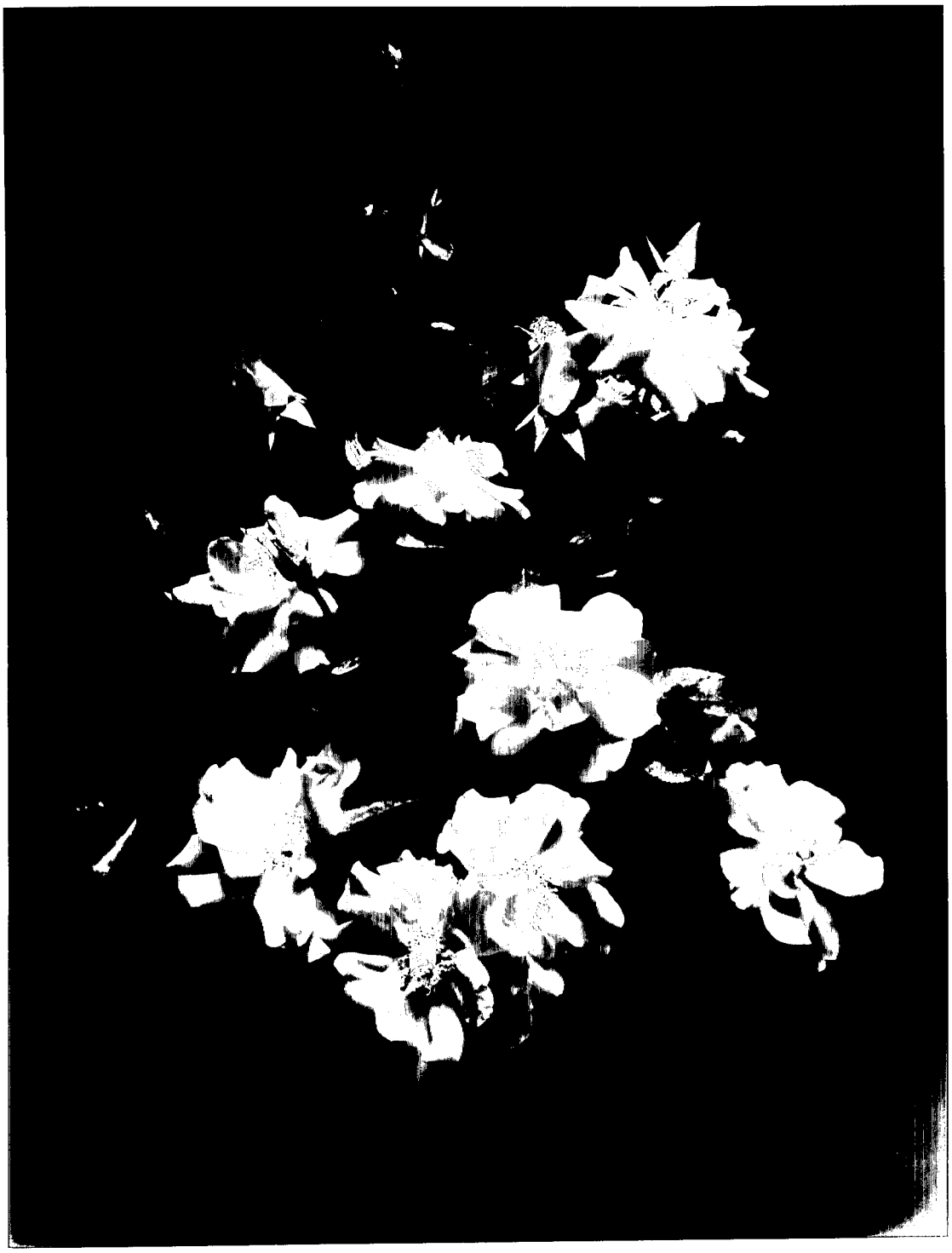

Buck

[11] Patent Number: Plant 5,760

[45] Date of Patent: Jul. 8, 1986

[54] ROSE PLANT NAMED BUCRED

[75] Inventor: Griffith J. Buck, Ames, Iowa

[73] Assignee: Iowa State University Research Foundation, Inc., Ames, Iowa

[21] Appl. No.: 672,698

[22] Filed: Nov. 19, 1984

[51] Int. Cl.[4] ..... A01H 5/00

[52] U.S. Cl. ..... Plt./1

[58] Field of Search ..... Plt./1, 28

*Primary Examiner*—Robert E. Bagwill

*Attorney, Agent, or Firm*—Tilton, Fallon, Lungmus

[57] ABSTRACT

A new variety of shrub rose plant having a profuse and continuous production of medium-sized flowers of bright red coloration, the plant being free branching, bushy, and erect in its growth habit and exhibiting an ability to survive Midwestern winter temperatures without weather protection. The plant also shows good field tolerance to foliar diseases such as Blackspot and Powdery Mildew.

1 Drawing Figure

BACKGROUND OF THE NEW PLANT

This new rose plant originated as a seedling resulting from a cross of the seed parent Carefree Beauty (Bucbi) (U.S. Plant Pat. No. 4,225) with an unnamed pollen parent obtained by crossing Marlena (U.S. Plant Pat. No. 2,700) with Pippa's Song (unpatented). The new variety was discovered by me at Iowa State University Horticulture Greenhouses, Ames, Iowa, in 1977 and resulted from breeding efforts commenced by me in 1949 at that University. The new plant was selected for propagation because of its continuous and profuse production of bright red flowers and especially because of its ability to survive winter temperatures in Iowa without weather protection and its notable resistance to foliar diseases. Since its discovery, this plant has been asexually reproduced by me, by budding, at Ames, Iowa, and propagated through successive generations to test its retention of the characteristics first observed. Continued propagation of this cultivar has demonstrated that its novel characteristics hold true from generation to generation and appear to be firmly fixed.

DESCRIPTION OF THE DRAWING

This new variety of rose plant is illustrated by the accompanying photographic drawing which, in full color, shows face and side views of fully-opened flowers and several other stages of the bloom from a tight bud, to a bud with sepals just cracked, to a newly-opened flower. The colors shown are as nearly true as can be reasonably expected to be reproduced by conventional photographic procedures.

DESCRIPTION OF THE NEW PLANT

The following is a description, in detail, of this new variety of rose plant with color designations according to The R.H.S. Colour Chart (R.H.S.C.C.) published by The Royal Horticultural Society of London, England, in collaboration of The British Colour Council (B.C.C.), with reference in some cases to the descriptive color designations adopted by the latter.

THE PLANT

Origin: Seedling.

Parentage:

*Seed parent.*—Carefree Beauty (Bucbi), U.S. Plant Pat. No. 4,225.

*Pollen parent.*—An unnamed variety obtained by crossing Marlena, U.S. Plant Pat. No. 2,700, with Pippa's Song (unpatented).

Classification:

*Botanic.*—*Rosa hybrida.*

*Commercial.*—Shrub Rose.

Form: Upright bush.

Height: About 90 to 125 cm.

Growth: Sturdy and vigorous.

Habit: Free branching and erect with strong canes and stems.

Foliage: Abundant quantity.

*Leaves.*—Texture: Smooth and leathery. Color: Arras Green 139A (R.H.S.C.C.) with petiole and rachis colored medium Grayed-Red 181A (R.H.S.C.C.) when young. Leaflets: 3 to 5 in number and of obovate shape.

Petioles: About 1.5 to 2 cm. in length.

Rachis: About 5.0 to 5.5 cm. in length.

Thorns and prickles: The plant lacks thorns, spines, and corms but it does have prickles that are about 0.7 to 1.4 cm. in length and have a coloration medium Gray-Red 181A (R.H.S.C.C.) when young, turning to light Grayed-Red 181C (R.H.S.C.C.) with age. On old canes the prickles are Beech Brown 165A (R.H.S.C.C.).

THE BUD

Size: Medium to medium-small in size, with a diameter of about 1.3 to 1.5 cm. and a length (depth) of about 2.5 to 3.0 cm.

Form: Ovoid, long, and pointed.

Opening: The buds open slowly.

Color: Guardsman Red 45A (R.H.S.C.C.), tinted with Current Red 46A (R.H.S.C.C.) when the sepals first divide, becoming Post Office Red 45B (R.H.S.C.C.) when the petals begin to unfurl.

Sepals: The sepals are spear-shaped and stand up, but curl back as the flower opens.

*Color.*—Inside — Light Medium-Green 138D (R.H.S.C.C.). Outside — Medium Green 138B (R.H.S.C.C.).

Calyx:

*Shape.*—Funnel-shaped, becoming globular.

*Size.*—Small, about 0.7 to 0.9 cm. in width and 0.9 to 1.2 cm. in length.

*Aspect.*—Smooth.

*Splitting.*—Calyx does not split.

Peduncle:

*Length.*—About 7 to 14 cm. long.

*Aspect.*—Hairy, prickly, and slender.

*Strength.*—Strong.

*Color.*—Varies from Medium Grayed-Red 181A (R.H.S.C.C.) to Medium Green 138B (R.H.S.C.C.) tinted with Medium Grayed-Red 181A (R.H.S.C.C.).

THE FLOWER

Blooming habit: Profuse and continuous from early to late season.

Size: Medium, about 7.5 to 8.5 cm. in diameter and 2 to 4.5 cm. in depth.

Borne: Singly and in clusters of 3 to 5 buds and flowers.

Shape: When bloom first opens, the flowers are cup-shaped, but form later becomes flat with petals recurving slightly.

Petalage:

*Number of petals.*—12 to 18.

*Arrangement.*—Imbricated.

*Form.*—Round-obovate.

*Texture.*—Soft and satiny.

*Color.*—Outer petals are Post Office Red 45B (R.H.S.C.C.) with white onglets at their bases. After full bloom, the color develops a bluish tint and lightens to light Rose Bengal 57B (R.H.S.C.C.). Inside petals are also 45B (R.H.S.C.C.), with the reverse sides of the petals being slightly lighter, Cherry Red 45C (R.H.S.C.C.).

Petaloids:

*Number.*—3 to 5.

*Size.*—About 2 to 3 cm. long, and about 2 cm. wide.

*Color.*—Post Office Red 45B (R.H.S.C.C.) with white streaks.

Persistence: The petals drop cleanly after full bloom.

Fragrance: Pleasantly sweet.

Lasting quality: About 4 to 5 days on the plant and about 5 to 6 days as a cut flower. The bloom appears unaffected by wet or hot weather.

REPRODUCTIVE ORGANS

Stamens:

*Anthers.*—Numerous, with a length of about 0.9 to 1.1 cm. and in a circular arrangement.

*Filaments.*—The filaments have a length of about 0.7 to 0.9 cm. and a color of Dresden Yellow 5B (R.H.S.C.C.).

*Pollen.*—The color of the pollen is Dresden Yellow 5B (R.H.S.C.C.).

*Pistils.*—Numerous, with a length of about 0.4 to 0.6 cm.

*Stigmas.*—Color is Dresden Yellow 5B (R.H.S.C.C.).

*Ovaries.*—Ovate with hispid achenes attached to the receptacle wall.

FRUIT

The fruit is semi-fertile and round or ovoid in form, with a color at maturity of Burnt Orange 31B (R.H.S.C.C.).

This rose plant resembles the Floribunda Rose Plant Marlena, one of its parents, in its floral traits, differing in appearance in its taller growth but profusely and consistently producing fine quality blooms similar to its parent. The plant is, however, exceptional in its ability to survive under adverse winter conditions and its field tolerance to foliar diseases such as Blackspot and Powdery Mildew.

I claim:

1. A new and distinct variety of rose plant substantially as herein shown and described, characterized by its profuse production of medium-size flowers of bright red coloration, its vigorous and free-branching growth habit, its ability to survive without protection under adverse winter conditions, and its resistance to foliar diseases.

* * * * *